US00PP14625P39

(12) United States Plant Patent
McNeilage et al.

(10) Patent No.: US PP14,625 P3
(45) Date of Patent: Mar. 23, 2004

(54) KIWI PLANT NAMED 'HORTGEM RUA'

(50) Latin Name: *Actinidia arguta*
Varietal Denomination: Hortgem Rua

(75) Inventors: Mark A McNeilage, Auckland (NZ); Ron A Beatson, Motueka (NZ); Elspeth A MacRae, Auckland (NZ)

(73) Assignee: The Horticulture and Food Research Institute of New Zealand, Limited, Palmerston North (NZ)

( * ) Notice: Subject to any disclaimer, the term of this patent is extended or adjusted under 35 U.S.C. 154(b) by 0 days.

(21) Appl. No.: 10/084,606

(22) Filed: Feb. 25, 2002

(65) Prior Publication Data

US 2003/0163860 P1 Aug. 28, 2003

(51) Int. Cl.[7] ..... A01H 5/00

(52) U.S. Cl. ..... Plt./156

(58) Field of Search ..... Plt./156

*Primary Examiner*—Bruce R. Campell
*Assistant Examiner*—June Hwu
(74) *Attorney, Agent, or Firm*—Greenlee, Winner and Sullivan, P.C.

(57) ABSTRACT

A new and distinct kiwi plant of the species *Actinidia arguta* (Sieb. & Zucc.) Planch. ex Miq. var. *arguta* is described. The variety results from a controlled pollination using a female *A. arguta* selection AAME01_01 (unpatented) and a male *A. arguta* selection AAME01_05 (unpatented). The fruit of this new variety has an attractive appearance (both internal and external) characterised by its green hairless, edible skin with red-centered flesh at maturity, small fruit size, oblong shape, and sweet aromatic taste. The new variety has been named 'Hortgem Rua'.

4 Drawing Sheets

Genus and species of plant claimed: *Actinidia arguta.*

BACKGROUND TO THE INVENTION

Kiwi plants in cultivation are mainly varieties of *A. deliciosa*, particularly 'Hayward' although some *A. chinensis* and *A. arguta* varieties are grown. *A. deliciosa* and *A. chinensis* are closely related, whereas *A. arguta* is classified in a separate section of the genus. *A. deliciosa* and *A. chinensis* varieties have large fruit (~100 g) with hair on the skin. The main varieties in New Zealand are 'Hayward' (*A. deliciosa*) and 'Hort16A' (*A. chinensis*). Fruit are usually cut and eaten with a spoon. *A. arguta* has small fruit (~10 g) with no hair on the skin. The skin is edible so these fruit can be eaten whole, like a grape.

All Actinidia species are dioecious, so female varieties have to be interplanted with male pollinizers to ensure fruit production.

*A. arguta* vines are deciduous and tend to grow vigorously in spring and summer when rapidly-growing shoots can intertwine and tangle if not managed. Vines do best in a mild temperate climate without late spring or early autumn frosts. They produce consistent heavy crops when grown in well-drained fertile soils and given regular irrigation in dry spells.

*A. arguta* flowers in spring (late October–early December) in New Zealand. Harvest of *A. arguta* fruit may occur between early February and late March in New Zealand depending on the selection and location of plantings. Compared to *A. deliciosa* and *A. chinensis, A. arguta* fruit require more careful handling during harvest and post-harvest procedures.

SUMMARY OF THE INVENTION

The new variety was selected from a population of seedlings derived from crossing the *A. arguta* selection AAME01_01 (unpatented) and a male *A. arguta* selection AAME01_05 (unpatented). This new variety was created during the course of a planned plant-breeding program, which was initiated during 1987 at HortResearch in Auckland, New Zealand. The controlled cross was made in November 1987. Seeds were sown in autumn (March) 1988 and seedlings were selected from this cross and were planted out in the field at HortResearch Kumeu Research Orchard in spring (October) 1988. The seedlings first fruited in February–March 1991. Promising female seedlings were clonally propagated into a two-site replicated trial in 1995 and 'Hortgem Rua' (breeding code E4I6) was selected after storage and sensory evaluation in 1998.

The new variety can be asexually reproduced as cuttings or by grafting or budding on to seedling or cutting-grown rootstocks of *A. arguta*. Trial plantings as cuttings established in 1995 at the HortResearch Te Puke and Nelson Research Centres and on seedling rootstocks established in 1998 at these sites have shown that the unique combination of characters come true to form and are established and transmitted through succeeding asexual propagations.

BRIEF DESCRIPTION OF THE ILLUSTRATIONS

Figure 1:
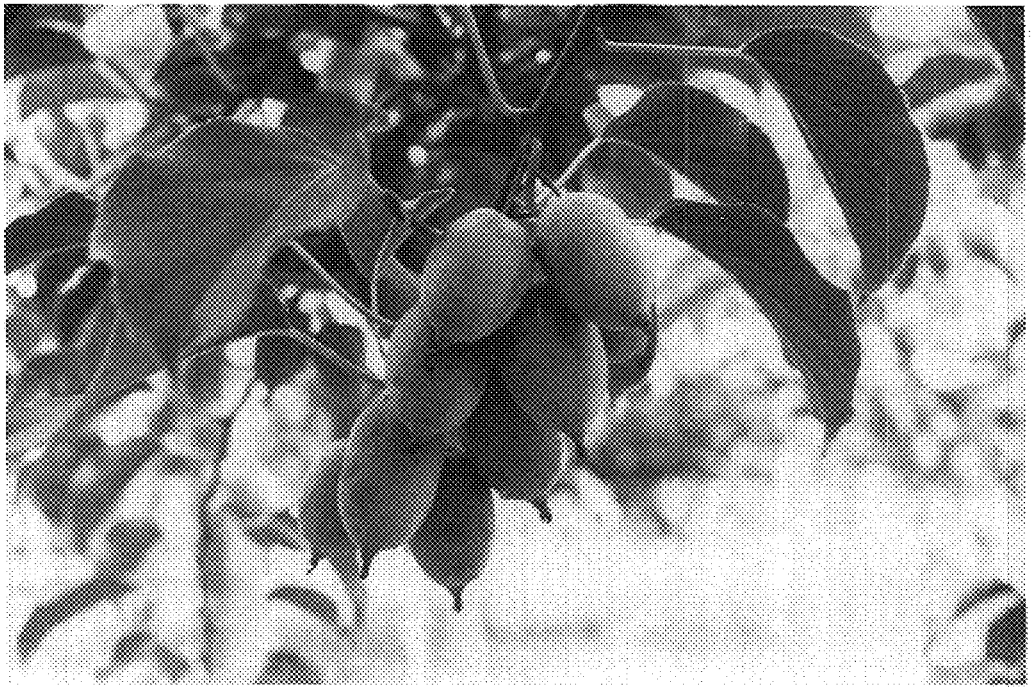
FIG. 1 shows typical fruit of the variety 'Hortgem Rua' in the orchard.
Figure 2:
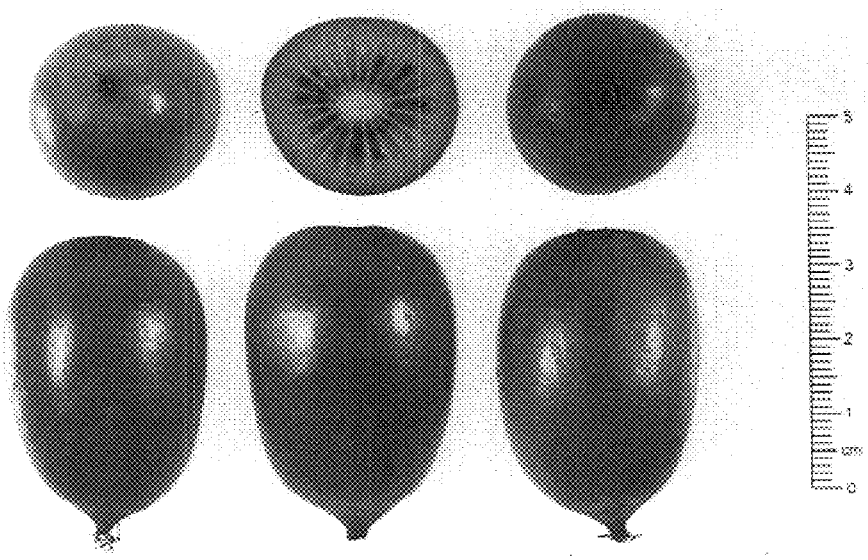
FIG. 2 shows typical fruit of the variety 'Hortgem Rua' in the studio.
Figure 3:
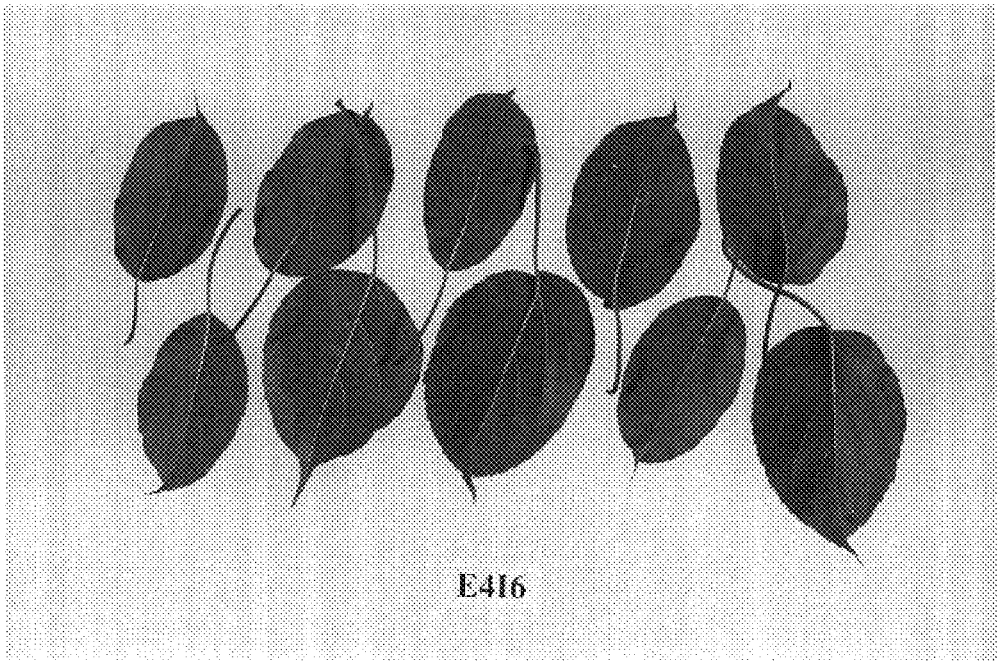
FIG. 3 shows leaves of the variety 'Hortgem Rua'.
Figure 4:
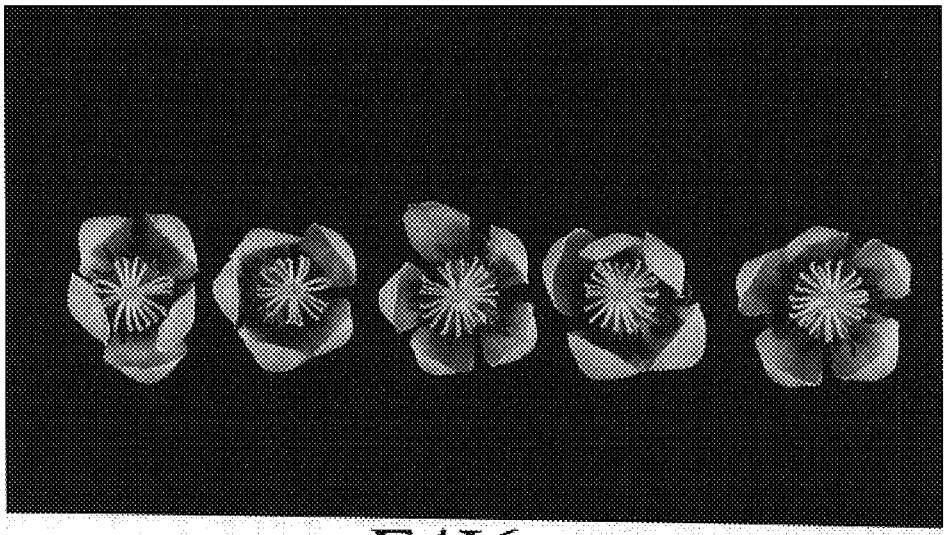
FIG. 4 shows flowers of the variety 'Hortgem Rua'.

Photographs of fruit were taken after the normal harvest date and are depicted in colors as nearly true as is reasonably possible to make the same in a color illustration of this character. Fruit skin color may vary depending upon extent of exposure to direct sunlight.

MORPHOLOGICAL DESCRIPTION OF THE VARIETY

The following is a detailed description of the new variety. The specimens described were grown at HortResearch Te Puke Research Orchard, Bay of Plenty, New Zealand. The observations were made in the 1998 season on vines established in 1995 that were three years old at the time, and managed under standard orchard practice.

Horticultural terminology is used in accordance with revised UPOV guidelines for kiwi. All dimensions in millimeters, weights in grams (unless otherwise stated). Color chart: R.H.S. Color Chart, The Royal Horticultural Society, London (3$^{rd}$ ed. 1995).

PLANT AND FOLIAGE

This female, tetraploid, plant expresses a twining habit of medium vigour. Hairs are absent from the young shoot. Anthocyanin (red) coloration of the growing tip is near Red-purple 59A. Otherwise the young shoot is near Yellow-green 144A in color. The stem of the plant is thin; with the range of diameters observed approximately 4.0 to 12.0 mm. The stem color on the exposed side ranges between near Greyed-orange 166A and near Greyed-orange 166B, and the bark is moderately rough. Lamellate pith is present. The lenticels are average in number and density (approximately 15–30/cm$^2$), and near Greyed-orange 166B in color on the upper surface and near Greyed-white 156C in color on the lower surface. Typically lenticels measure approximately 0.88 mm in length and 0.75 mm in width. Bark on the laterals is similarly colored to that on the stem and the laterals are absent of hairs. The proximal face of the bud support is perpendicular and a bud cover is present. Typically the bud support is approximately 4.73 mm in diameter; the leaf scar is deep. Dormant bud is small in diameter (ranging approximately 0.7 to 4.0 mm).

The mature leaf is broad ovate in shape and typically averages approximately 91 mm in length, and approximately 50 mm in width. Leaves are typically in an upward pose; upfolded to concave shape in cross section, with serrate indentations of the margin, and medium glossiness on the upper surface. Puckering or blistering of the leaf surface is absent or very weak. The leaf basal lobes are arranged far apart (the width between the lobes being approximately 1.56 mm). The petiole length averages within the range approximately 23–25 mm, with medium size stipules. Hairs on the petiole are absent or very sparse and anthocyanin (red) coloration on the upper surface of the petiole is near Red 53A. The color of the leaf blade is green; within the range near Green 137A and near Green 139A on the upper surface; within the range near Green 138B and near Yellow-green 146B on the lower surface. Neither surface of the leaf exhibits glaucosity.

INFLORESENCE

The predominant number of flowers in the infloresence is three. The pedicel length typically averages about 27.6 mm, with sparse, very short (averaging approximately 0.29 mm in length) hairs. There are typically five sepals, small in size. These are near Grey-brown 199D in color with red (near Red 53A) pointed tips. The diameter of the terminal or king flower when fully open is small, averaging about 27.6 mm in diameter. The mean number of petals per flower is approximately 5. The petals are arranged overlapping and are near Green-white 157A in color when fully open. There are many stamens (ranging approximately 40–50 in number). The filament color is near Green 130D; the anther color varies within the range near Black 202A to near Grey 201B. The number of styles averages approximately 21.9 and they are arranged in a semi-erect attitude. The ovary is smooth.

FRUIT

The fruit are overall small to medium in size, averaging approximately 16.4 g (observed range approximately 14–18 g) in weight; approximately 37.4 mm in length; approximately 22.4 mm at maximum width. The general shape of the fruit is oblong; the stylar end being strongly protruding pointed; the shoulder on the stalk end being rounded. The shape of the fruit in cross-section at the median is oblate. The peduncle averages approximately 28.2 mm in length and approximately 3.9 mm in diameter.

The fruit skin is thin, smooth, and absent of hairs. The fruit exhibit green skin and green flesh throughout the fruit growth phase; fruit skin color at harvest (fruit still hard) is within the range near Green 140A to near Green 143B. Fruit color changes are evident during the ripening period; flesh color change typically commences approximately 109 days after anthesis. Flesh color change occurs as a progression from green to a more red color; this reddening typically occurring at the end of the fruit that softened first; from the stem end down. During ripening, the skin color is affected by the internal color changes: the color of the fruit skin at maturity for consumption being within the range near Red-purple 59A to Green 143A. The color of the outer pericarp at maturity for consumption is tends to be predominately green (within the range near Green 137A to near Green 141A; the inner pericarp (locules) exhibit predominately red coloration (within the range Red-purple 59A to Green 143A). Typically the number of locules averages approximately 19.1

The fruit core is medium in diameter (averaging approximately 5.5 mm at the largest diameter), is oblate in cross-section, and is near green white in color (within the range of near Yellow-green 150D and near Green-white 157B) at harvest. There is no woody spike.

Seed is small (maximum average diameter approximately 1.3 mm; maximum average length approximately 2.5 mm). The seed color in the flesh at fruit maturity is dark brown (near Brown 200B) and brownish-orange when dry (within the range near Greyed-orange 172B and near Greyed-orange 175C).

The fruit flesh is tender at maturity for consumption and fruit sweetness (Brix level) averages approximately 12.4% (observed range approximately 7.4 to 15.8 Brix). Fruit aroma is evident. Dry matter content averages approximately 18.6% (average maximum dry matter content observed 20.2%). Typically fruit have demonstrated a storage life of 3–5 weeks at 0° C. in air storage.

CULTIVATION

Flowering commence early November in New Zealand and is approximately 10 days in duration. The time of fruit maturity for harvest (at nominated Brix level) occurs approximately February in New Zealand.

Observations made on cutting-grown plants growing at HortResearch Te Puke Research Centre, New Zealand demonstrated the following horticultural characteristics.

Cropping: Young vines of the new variety are precocious, beginning to bear in their second year and are expected to reach full capacity at about 7 years. The storage life of the fruit is 3–5 weeks at 0° C., when stored in unventilated containers in air storage.

Yield and fruit size: data from harvesting all fruit from 3 year old vines in early February 1998.

Mean fruit number: 389.

Mean yield: 6.1 kg.

Proportion of fruit <6 g: 2%.

Proportion of marked fruit: 38%.

It is anticipated mature, well-managed vines would yield approximately 3000 fruit per vine with a mean fruit weight of 14 g and mean yield per vine of 420 Kg.

No pest and disease resistance has been observed. The plant hardiness range (according to the American zone classification) has not been determined. Under New Zealand conditions, the plants are grown in areas that experience some winter cold and frost, estimated to be equivalent to the minimum temperature range of zones 8 and 9.

We claim.

1. A new and distinct kiwi plant of the species *A. arguta* substantially as herein described and illustrated, characterised by its green hairless, edible skin with red-centered flesh at maturity, small fruit size, oblong shape, and sweet aromatic taste.

* * * * *

E4I6

UNITED STATES PATENT AND TRADEMARK OFFICE

CERTIFICATE OF CORRECTION

PATENT NO. : PP 14,625 P3
DATED : March 23, 2004
INVENTOR(S) : McNeilage et al.

It is certified that error appears in the above-identified patent and that said Letters Patent is hereby corrected as shown below:

Column 6,
Line 3, delete "420 Kg." and replace with -- 42 kg. --

Signed and Sealed this

Thirtieth Day of November, 2004

JON W. DUDAS
*Director of the United States Patent and Trademark Office*